(12) United States Patent
Lemercier et al.

(10) Patent No.: US 6,180,141 B1
(45) Date of Patent: Jan. 30, 2001

(54) COMPOSITE GEL MICROPARTICLES AS ACTIVE PRINCIPLE CARRIERS

(75) Inventors: Alain Lemercier, St Bonnet de Mure; Rémi Meyrueix; Sylvain Huille, both of Lyons; Gérard Soula, Meyzieu, all of (FR)

(73) Assignee: Flamel Technologies, Venissieux Cedex (FR)

( * ) Notice: Under 35 U.S.C. 154(b), the term of this patent shall be extended for 0 days.

(21) Appl. No.: 09/147,032

(22) PCT Filed: Mar. 14, 1997

(86) PCT No.: PCT/FR97/00471

§ 371 Date: Jan. 4, 1999

§ 102(e) Date: Jan. 4, 1999

(87) PCT Pub. No.: WO97/34584

PCT Pub. Date: Sep. 25, 1997

(30) Foreign Application Priority Data

Mar. 15, 1996 (FR) .................................................. 96 03546

(51) Int. Cl.[7] ...................................................... A61K 9/14
(52) U.S. Cl. ........................... 424/489; 424/499; 424/493; 424/491; 424/479; 424/497
(58) Field of Search ...................................... 424/489, 491, 424/464, 78.01, 465, 490

(56) References Cited

U.S. PATENT DOCUMENTS 4,904,479 * 2/1990 Illum .................................... 424/490

* cited by examiner

Primary Examiner—Thuaman K. Page
Assistant Examiner—William E. Benston, Jr.
(74) Attorney, Agent, or Firm—Dennison, Scheiner, Schultz & Wakeman (57) ABSTRACT

The invention relates to vectors for delivering medicinal, nutritional, plant-protection or cosmetic active principles, these delivery particles being of small, controllable and adjustable particle size, which protect the active principle, and being biocompatible, biodegradable, non-immunogenic, stable and free of solvent. The particles do not denature the active principle and allow the active principle to be released. The microparticles of the invention are of a cohesive structure made of a physicochemically stable and integral composite gel which includes an oil such as coconut oil, an aqueous phase and a linear, non-crosslinked copolyamino acid of Leu/Glu type (random or diblock). The microparticles have a controllable and adjustable size of between 0.05 and 500 $\mu$m.

21 Claims, 3 Drawing Sheets

COMPOSITE GEL MICROPARTICLES AS ACTIVE PRINCIPLE CARRIERS

This application is a 371 of PCT/FR97/00471 filled Mar. 14, 1997.

BACKGROUND OF THE INVENTION

The field of the present invention is that of vectors which are useful for the administration of active principles (APs), preferably medicinal or nutritional active principles, in particular via the oral, nasal, vaginal, ocular, subcutaneous, intravenous, intra-muscular, intradermal, intraperitoneal, intracerebral, parenteral, etc. route. These vectors allow the protected delivery of the APs into the body, to their site of action. They are intended to improve the bioavailability of APs. These vectors can be, for example, systems for the sustained release of APs.

The APs with which the invention is more particularly, but not exclusively, concerned are, for example, proteins, glycoproteins, peptides, polysaccharides, lipopolysaccharides, oligonucleotides and polynucleotides.

More specifically, the present invention relates to delivery particles (DP)—advantageously of submicron and/or micron type—for delivering APs, in particular medicinal APs.

Besides medicinal and nutritional APs, the invention also relates to plant-protection and cosmetic APs.

The present invention is directed toward both naked particles per se, and AP delivery systems, consisting of particles loaded with the AP(s) considered.

The invention also relates to a process for preparing the said particles.

PRIOR ART

Progress in genetic engineering and biotechnology, as well as the related discoveries of biologically active peptide, proteinic and genetic tools have allowed the development of novel medicinal active principles (APs) offering high intrinsic activity and high selectivity. On the other hand, these APs are easily degraded in the body before reaching their therapeutic site of action, and their bioavailability is consequently very low. In the case of oral administration, the gastrointestinal tract constitutes a formidable chemical and physical barrier for an AP which must, on the one hand, withstand degradation by the digestive system and, on the other hand, pass through the gastrointestinal epithelial membrane. In this respect, reference may be made, for example, to the review by M. J. Humphrey (Delivery System for Peptide Drugs, edited by S. Davis and L. Illum, Plenum Press, N.Y., 1986), which gives an account of the low bioavailability of peptides and of peptides administered orally.

Naturally, these mishaps of delivery and residence in the body are not limited to proteins, but also affect APs formed by genetic tools (oligonucleotides, polynucleotides, plasmids) liable to be used in genetic engineering techniques.

To overcome this, it has been proposed to encapsulate APs in AP delivery particles, also referred to as DPs. The advantage of these encapsulation techniques is that they protect and/or deliver the AP up to its therapeutic site of action, by keeping it safe from attack by the body, in order to increase its bioavailability.

Of all the materials which can be envisaged for encapsulating APs, polymers are increasingly used on account of their intrinsic properties.

As regards the list of specifications which it is desired to obtain for such DPs, this is particularly demanding and comprises, in particular, the following specifications:

1—It should, advantageously, be possible to obtain DPs with an average diameter of between a fraction of a micron and a few microns, with a narrow particle size distribution, so as to be able to adapt the DP particle size to the mode of administration selected and/or the therapeutic site targeted. For example, if a mucosal immunization via the oral route is desired, the DP size should be between 0.5 $\mu$m and 10 $\mu$m in order for the DPs to be able to penetrate the Peyer plates and reach the lymphoid tissues. In the case of subcutaneous administration, it is advantageous to have DPs larger than 10 $\mu$m in size in order for the particles not to enter into the general circulation, in which they are rapidly internalized by the reticuloendothelial system, but for them to diffuse gradually from their site of injection.

This specification implies controlling the size of the DPs, as regards both the DP particle size distribution and their average diameter, which represents a very intricate operation in technological terms.

2—It is desirable for the DPs to protect the AP up to the site of release. For example, in an oral administration of an AP formed of a vaccine, the vaccine would be successfully protected throughout the gastrointestinal tract.

3—It is preferable for the polymer which forms the DPs to be biocompatible and biodegradable and, better still, for it to be metabolized into products that are non-toxic to the body.

4—It is also advantageous for the polymer which forms the DPs not to induce an immune response (immunogenic).

5—The DPs are expected to allow the controlled and sustained release of the AP.

6—Lastly, it is also preferable for the DPs to be obtainable by a process which does not denature the AP. Thus, the use of organic solvents and/or high temperatures should be ruled out.

Many prior technical approaches have attempted, unsuccessfully, to satisfy all of these specifications. The solutions provided hitherto are thus only partial and incomplete.

In all of these unfruitful approaches of the prior art, several constituent base materials have been envisaged for the delivery particles. These materials can be biocompatible polymers, such as proteins and/or polymers of $\alpha$-hydroxy acids (polylactic and/or glycolic acids) and/or poly(alkyl cyanoacrylates) and/or polyorthoesters and/or fatty substances (oils—fats).

The DPs (microspheres or microcapsules) of protean nature are usually obtained by drastic crosslinking treatments using glutaraldehyde-type chemical agents or by raising the temperature. It goes without saying that such treatments necessarily entail denaturing of a large number of active principles. What is more, the toxicity of glutaraldehyde-type crosslinking agents is particularly unfitting in pharmaceutical applications. As examples of such known microparticles, mention may be made of those disclosed in patent application EP 0,363,921. The particles according to that application are obtained by complex coacervation of a synthetic polyamino acid and an anionic polymer, in aqueous solution, by adjusting the pH. The polyamino acid is an amphiphilic copolymer based on glutamic acid and lysine, whereas the anionic polymer is a water-soluble polysaccharide, such as gum arabic. These particles are given cohesion by crosslinking the coacervate using glutaraldehyde. Besides the toxicity and degradation problems of the APs mentioned above, it should be noted that the polymers in the coacervate according to EP 0,363,921 suffer from an immunogenic nature.

Protean microparticles or microparticles based on biocompatible and biodegradable polymers can also be prepared by standard emulsion techniques.

In this respect, mention may be made, for example, of patent applications WO 91/06 286 and WO 91/06 287 which describe processes for the formation of particles in emulsion, these processes using, as polymer:

either a hydrophobic protein chosen from collagen, casein, keratin and, preferably, prolamines, or a biocompatible and biodegradable polymer, such as poly(lactics) or poly(orthoesters).

The AP can be hydrophobic or hydrophilic but, in the latter case, the double-emulsion technique is recommended. The size of the microparticles is about 100 μm and preferably between 50 nm and 100 μm.

Patent application WO 89/08 449 also makes reference to encapsulation by emulsion, in order to incorporate APs into poly(lactic) microparticles less than 10 μm in size. Moreover, it is pointed out in that document that this size is a maximum limit for absorption across the lymphoid tissues of mucous membranes (oral, nasal, rectal and ophthalmological administrations).

The emulsion techniques are very appealing in principle, since they allow most of the APs to be used in microparticles whose particle size can be controlled to sizes of about 1 μm. However, in these techniques, organic solvents are used to dissolve the polymers which make up the particles. These solvents are, for example, ketones, alcohols, amides or mixtures thereof. Unfortunately, in addition, it turns out that these solvents can be denaturing, in particular for peptide or polypeptide APs.

Mention will also be made, with respect to the constituent polymers of poly-α-hydroxy acid type (polylactic and/or glycolic type) of a problem of accumulation in vivo which is liable to give rise to rejection effects.

Biocompatible DPs formed in aqueous solution without excessively raising the temperature, and referred to as proteinoids, are also known. These DPs were described as early as 1970 by W. Fox and K. Dose in "Molecular Evolution and the origin of Life", Ed. Marcel Dekker Inc. (1977).

Taking inspiration from these studies, patent application Wo 88/01 213 proposes a proteinoid-based AP delivery system. The polymer used is a mixture of artificial polypeptides obtained by thermal condensation of natural or synthetic amino acids and/or of small peptide chains. The mode of condensation chosen leads to branched oligomers which are thus very sparingly soluble. A selection is then made by filtering these branched oligomers, in order to recover the water-soluble fractions. This fraction is necessarily composed of branched reticulates of very low mass. The microparticles according to that invention are obtained by changing the pH which causes precipitation of the branched oligomers as proteinoids.

When the solution in which the precipitation is carried out contains APs in solution, some of them are entrained into the proteinoid when it is formed. The drawbacks of this system are:

a low degree of encapsulation, a method of synthesis by lowering the pH, an intricate process for purifying the polymers, an irregular (non-alpha-peptide) amino acid sequence due to the mode of synthesis which makes it possible to assert only that the enzymatic degradation reactions will be identical to those of an α-polyamino acid, lastly, the use of a large number of different amino acid monomers, which can induce an immune response.

Patent application WO 93/25 589 relates to an improvement to the process for the synthesis of proteinoids by thermal condensation of amino acids. The same drawbacks as those associated with the subject-matter of the parent application mentioned above are found.

The nanocapsule-type microparticles described in patent application EP 0,608,207 and whose wall is based on poly(alkyl 2-cyanoacrylate), are mentioned here merely as a matter of interest, since the toxicity of the residues of the monomers used is clearly detrimental for the delivery of APs in man and/or animals. Moreover, little is known about the elimination of the residues of such polymers.

Now, as regards DPs of essentially lipidic or hydrophobic nature, several types of systems may be listed, namely:

liposomes, solid lipid particles (SLPs), multi-chamber lipid vesicles (MCLVs), supercooled molten particles (SMPs), lipid emulsions, and particles of the lipid matrix carrier (LMC) type.

Liposomes are spherical colloidal structures comprising an aqueous internal phase enveloped by one or more phospholipid bilayers. Liposomes are known as delivery particles.

A first drawback of liposomes is their instability in biological fluids and the high rate of release of the AP which they may contain. Reference may be made in this respect to the article by Kim et al., Biochim. Biophys. Acta, 728, 339–348, 1983.

A second drawback of liposomes is that they only allow a low level of filling with AP.

A third drawback of liposomes relates to their instability on storage.

A fourth drawback of liposomes is associated with the poor reproducibility of their manufacture and, in particular, their mediocre ability to trap APs.

There is a wealth of patent literature regarding liposomes. Mention will be made, as a matter of interest, of the following patents: U.S. Pat. Nos. 3,993,754, 4,235,871, 4,356,167 and 4,377,567.

International patent application PCT WO 94/20 072 describes solid lipid particles (SLPs) of non-spherical form, consisting of a crystalline lipid matrix which is solid at ambient temperature. The high-melting lipids concerned are preferably triglycerides (θ fusion=30–120° C.). In suspension, these SLPs can be stabilized by amphiphilic, ionic or nonionic compounds. These amphiphilic stabilizing compounds can be phospholipids, sphingolipids, glycosphingolipids, physiological bile salts, saturated or unsaturated fatty acids, fatty alcohols, methoxylated fatty acids or alcohols, as well as esters thereof and ethers thereof, polyether alkyloaryl alcohols, esters and ethers of sugars or of sugar-alcohols with fatty acids or fatty alcohols, acetylated or ethoxylated mono- or diglycerides, block copolymers of polyoxyethylene and of polyoxypropylene oxide, ethoxylated sorbitan ethers or esters, amino acids, polypeptides, proteins (gelatins, albumins), as well as mixtures of the abovementioned compounds.

On account of their crystalline solid nature, these SLPs necessarily include a step of melting at high temperature, during their formation and the incorporation of the AP. It has already been pointed out that heating to high temperatures is harmful to certain sensitive APs. In addition, given the exclusively lipidic nature of SLPs, they turn out to be unsuitable for hydrophilic APs. Lastly, when a hydrophobic AP different in nature from the one forming the matrix of the SLP is concerned, the incorporation yields are extremely low, of the order of a few %.

International patent application PCT WO 95/13 796 describes internal aqueous multi-chamber lipid vesicles (MCLVs). These DPs are novel with respect to liposomes by virtue of their non-concentric multi-chamber structure and their aqueous content. The said aqueous chambers are each formed of a membrane formed of a lipid bilayer which defines a sphere.

In order to prepare these MCLVs, a neutral lipid of plant oil, animal fat or tocopherol type is used, as well as an amphiphilic lipid which has a large negative charge, e.g. phosphatidylserine. These two types of lipids are dissolved in an organic solvent to which is added an aqueous solution comprising the AP to be encapsulated, so as thus to form a water-in-oil emulsion. This emulsion is completed by adding an agent for delaying the release of the AP. A second emulsification is then carried out by adding a second aqueous solution containing at least one nonionic osmotic agent and an acid-neutralizing agent of low ionic strength. After stirring, spherules of solvent containing many aqueous droplets are obtained. On evaporating the solvent, these spherules are converted into MCLVs. The inner aqueous chambers are thus in suspension in the secondary aqueous solution and not in the chloroform which has been eliminated.

Like its alternative forms, this double-emulsion technique can be criticized in that it involves toxic organic solvents whose absence, in trace form, from the final microparticles cannot be guaranteed.

International patent application PCT WO 95/05 164 describes particles of ubidecarenone or of other substances which have poor water solubility, in which this or these substances with poor water solubility are in the "supercooled molten" state, i.e. they are in a state similar to the liquid state at a temperature below their melting point. These particles, also known as SMPs, require the use of an amphiphilic stabilizer (lecithin) when they are suspended in an aqueous liquid. These stabilizers are the same as those described in patent application PCT WO 94/20 072 which concerns SLPs. The supercooled molten substance forming the particle has a melting point of about 70° C. These are thus fats rather than oils that are liquid at ambient temperature. The fatty substances capable of forming such a molten substance are chosen from vitamins, sterols and triglycerides, for example.

These SMPs are obtained by melting the substance intended to form the supercooled molten substance. The amphiphilic compound is then dispersed in this molten substance. Water is then added and the mixture is subjected to homogenization/stirring at high speed, while at the same time keeping the reaction temperature above the melting point of the substance used. A dispersion of SMP in a continuous aqueous phase is finally obtained. The SMP microparticles are free, or virtually free, of water.

Such vectors have the drawback of being specific and exclusive to hydrophobic APs. In addition, the high temperatures required to carry out the process for preparing these SMPs can be harmful to the APs.

Delivery systems involving lipid emulsions consisting of droplets of liquid oil dispersed in an aqueous phase and stabilized by an interfacial film of emulsifier (lecithins) are also known. AP delivery using DPs, constituting the heterogeneous phase of the lipid emulsion, is described in international patent application PCT WO 91/02 517. The cohesion, integrity or stability of such DPs is precarious or fragile, since these DPs have no physical existence, i.e. they do not form definite substances outside of the emulsion medium. Once the equilibrium established by the surfactant is disturbed, the droplets of liquid oil coalesce and disappear. Consequently, these lipid emulsions offer very few concrete measures in AP delivery.

U.S. Pat. No. 4,610,868 relates to a novel type of lipid DP, which can be described as being a globular structure formed of a lipid matrix. These DPs, also known as LMCs, are between 0.5 $\mu$m and 100 $\mu$m in size. The base constituents of the LMCs are a hydrophobic compound, an amphiphilic compound and, optionally, an AP accompanied by water if the latter is of water-soluble nature.

The hydrophobic compound is preferably a triglyceride-based oil, such as corn oil or coconut oil. Sterols may also be suitable as hydrophobic compounds.

The amphiphilic compounds recommended are those of lipidic nature, such as phosphoglycerides and, more particularly, phosphatidylcholine from egg yolk.

The preparation of these LMCs involves an organic solvent, such as acetone or ethanol. According to a specific embodiment of the process for preparing these LMCs, a water-in-oil emulsion—obtained from phosphatidylcholine oil, water and water-soluble APs—is extruded into the organic solvent with stirring. The LMCs are generated at the moment that the W/O emulsion is introduced into the solvent. When the AP is hydrophobic, the mixing of amphiphilic oil and of AP takes place in the organic solvent, the said mixture then being extruded into an aqueous phase.

For water-soluble APs, it can be envisaged to totally eliminate the aqueous phase and to extrude the oil+ amphiphile+AP mixture into the organic solvent. After elimination of the organic or aqueous solvent, LMCs are recovered which, according to the patent, are described as resembling droplets of oil which do not coalesce.

These LMCs have the major drawback of requiring the use of solvents during their preparation, and it is known that the presence of solvent, even in trace amounts in DPs, is particularly undesirable. The exclusively lipidic nature of LMCs will be stressed. Lastly, it should be considered that the process for obtaining the LMCs is relatively complex and hardly convenient to carry out industrially (extrusion into a solvent).

SUMMARY OF THE INVENTION

In this state of understanding, one of the essential aims of the present invention is to provide DPs, in particular submicron-sized and micron-sized DPs, based on lipids and which can serve as vectors for an active principle (AP), in particular a medicinal and/or nutritional AP, in order to administer the said AP to a human or animal body, these DPs fully satisfying the list of specifications given above and repeated below:

1—It should, advantageously, be possible to obtain DPs with an average diameter of between a fraction of a micron and a few microns, with a narrow particle size distribution, so as to be able to adapt the DP particle size to the mode of administration selected and/or the therapeutic site targeted. For example, if a mucosal immunization via the oral route is desired, the DP size should be between 0.5 $\mu$m and 10 $\mu$m in order for the DPs to be able to penetrate the Peyer plates and reach the lymphoid tissues. In the case of subcutaneous administration, it is advantageous to have DPs larger than 10 $\mu$m in size in order for the particles not to enter into the general circulation, in which they are rapidly internalized by the reticuloendothelial system, but for them to diffuse gradually from their site of injection.

This specification implies controlling the size of the DPs, as regards both the DP particle size distribution and their average diameter, which represents a very intricate operation in technological terms.

2—It is desirable for the DPs to protect the AP up to the site of release. For example, in an oral administration of an AP formed of a vaccine, the vaccine would be successfully protected throughout the gastrointestinal tract.

3—It is preferable for the polymer which forms the DPs to be biocompatible and biodegradable and, better still, for it to be metabolized into products that are non-toxic to the body.

4—It is also advantageous for the polymer which forms the DPs not to induce an immune response (immunogenic).

5—The DPs are expected to allow the controlled and sustained release of the AP.

6—Lastly, it is also preferable for the DPs to be obtainable by a process which does not denature the AP. Thus, the use of organic solvents and/or high temperatures or drastic pH changes should be ruled out.

Another essential aim of the invention is to provide lipid-based DPs which are stable on storage, irrespective of the external medium, i.e. which retain their physical integrity equally well in a continuous phase formed of water, formed of an aqueous solution or formed of an organic solvent, such that they should not have a tendency to coalesce.

Another essential aim of the invention is to provide lipid-based DPs which have a controllable and adjustable average particle size.

Another essential aim of the invention is to provide DPs which are simple to prepare (non-corrosive pH), stable at any pH between 2 and 13, and non-immunogenic.

Another essential aim of the invention is to provide lipid-based DPs which can be made industrially and in a cost-effective manner and which can be filled with either hydrophilic or lipophilic AP to high filling levels.

Another essential aim of the invention is to provide a process for the preparation of lipid-based DPs which can be used as AP vectors, the said process needing to be cost-effective, simple to carry out, non-denaturing for the APs and also needing to allow fine control of the average particle size of the particles obtained.

Another essential aim of the invention is the use of the said particles for the preparation of medicaments (e.g. vaccines) and/or nutrients, in particular for oral, nasal, vaginal, ocular, subcutaneous, intravenous, intramuscular, intradermal, intraperitoneal, intracerebral or parenteral administration of active principles such as proteins, glycoproteins, peptides, polysaccharides, lipopolysaccharides, oligonucleotides and polynucleotides.

Another essential aim of the invention is to provide a medicament of the type having a system with sustained release of AP, which is biocompatible and which affords high availability of the AP.

The aims relating to the products, inter alia, are achieved by the present invention, which relates to particles, in particular for the delivery of active principle(s), of the type based on microparticles which can be used as active principle (AP) vectors, characterized:

*α* in that they each have a cohesive structure made of physicochemically stable and integral composite gel,

*β* in that their cohesion is derived from the presence of the following three compounds:
(I) oil,
(II) an aqueous phase,
(III) and at least one linear, non-crosslinked, synthetic copolyamino acid comprising at least two different types of amino acid comonomers: hydrophilic $AA_i$ and hydrophobic $AA_0$,

*γ* and in that they have an average size which is controllable and adjustable over a range less than or equal to 500 μm, preferably to 200 μm, and even more preferably between 0.05 and 100 μm.

It is to the Applicant's credit to have developed these partially lipidic microparticles by, on the one hand, selecting specific constituent products, namely oil, water and specific copolyamino acid, and, on the other hand, developing a procedure for obtaining the said microparticles which leads, entirely surprisingly and unexpectedly, to a colloidal suspension of well-differentiated and extremely stable cohesive particles.

The stability is indeed one of the most surprising of the novel characteristics of the particles according to the invention, since they retain their integrity and their differentiated nature both in a liquid medium, irrespective of the pH of the medium, and in the form of lyophilysate. In other words, this means that they can be isolated by filtration or decantation (e.g. by centrifugation), without coalescing. They thus form species of composite gel type, which have their own identity and existence, irrespective of the medium in which they are stored.

For the purposes of the present invention, the term "composite gel" denotes or refers to a notion of a physical gel based on water, oil and polymer.

The DPs according to the invention are, moreover, biovectors that are capable of including any active principle, irrespective of its hydrophilic or hydrophobic nature, and of delivering it inside the body. These DPs are biovectors which are all the more suitable:

since they are non-immunogenic, biodegradable and free of toxic structuring and/or manufacturing products, even in trace amounts (solvents, glutaraldehyde), and since their size (particle size) can be controlled over a wide range.

In conclusion, DPs are stable and cohesive microparticles. They do not coalesce, in contrast with droplets of emulsion.

DETAILED DESCRIPTION OF THE INVENTION

Figure 1:
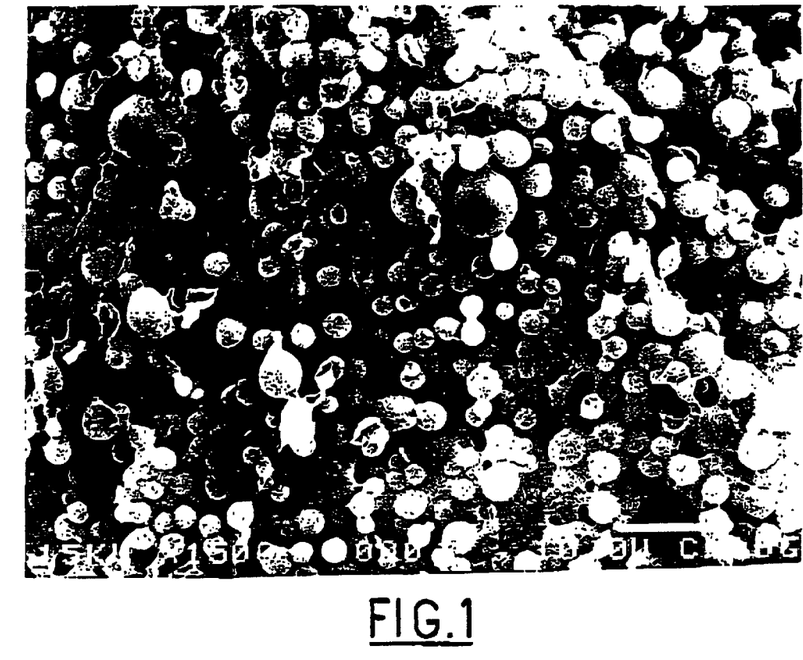
FIG. 1 is a scanning electron microscopy (SEM) photograph of the composite gel DPs prepared in Example 4, magnification: 1500x.
Figure 2:
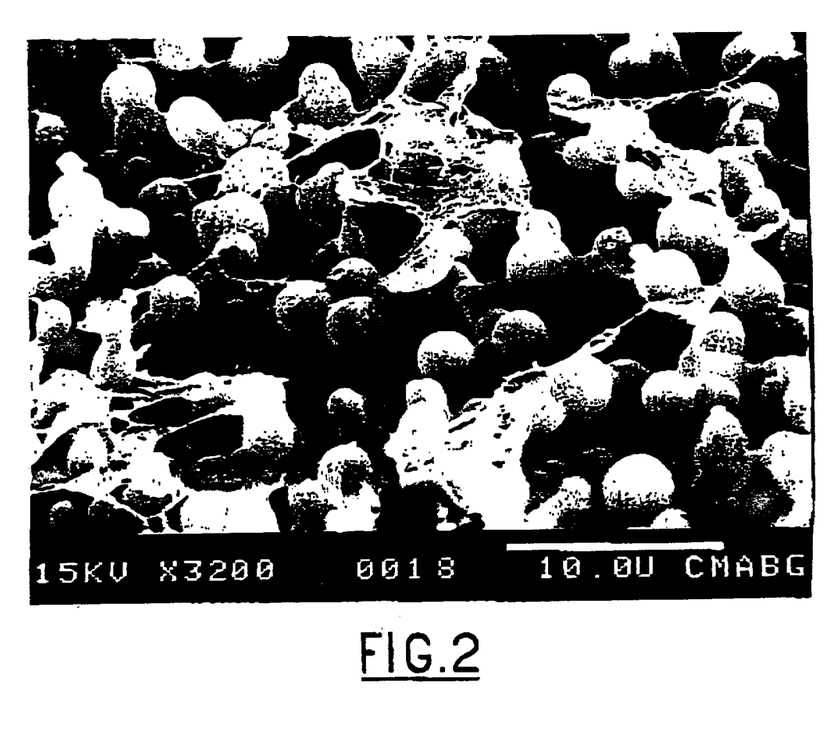
FIG. 2 is a scanning electron microscopy (SEM) photograph of the composite gel DPs prepared in Example 5, magnification: 3200x.

The morphology of these cohesive DPs according to the invention is seen clearly in the scanning electron microscopy (SEM) photographs given in the attached FIGS. 1 and 2. The description of these SEM photographs is repeated below, in particular in the examples. However, it can already be noted that these composite gel DPs are more or less spherical in shape and of smooth appearance. They are well differentiated from each other.

As regards their structure, it is possible to say that it is neither a leaflet arrangement of the type found in liposomes, nor is it simple droplets of heterogeneous phase of an O/W or W/O emulsion.

In the absence of tangible elements to characterize their structure, the Applicant has been able to define these composite gel DPs by means of particular functional features and, more specifically, behavioral features of these DPs from discriminating technical evaluation tests.

Thus, the *α* characteristics of the DPs targeted above are reflected by at least one of the following functional properties:

$α_1$—absence of coalescence of the microparticles after a lyophilization treatment, this non-coalescence being reflected by a conservation of the particle size distribution, in particular of the D[4.3] in a proportion of ±20%, after rehydration according to a test $α_1$;

$\alpha_2$—absence of coalescence on centrifugation, reflected by a conservation of the particle size distribution, and in particular of the D[4.3] in a proportion of ±20%, according to a test $\alpha_2$;

$\alpha_3$—resistance to pH variations, reflected by a conservation of the particle size distribution of the microparticles and, in particular, of the D[4.3] in a proportion of ±20%, after exposure to pHs of 3 and 13, according to a test $\alpha_3$;

$\alpha_4$—absence of coalescence in dispersion in a buffered aqueous solution, reflected by a conservation of the particle size distribution of the microparticles, in particular of their D[4.3] in a proportion of ±20%, for storage times of greater than or equal to 3, 9 and 18 months at temperatures of 37° C., ambient and 4° C. respectively, according to a test $\alpha_4$.

The tests $\alpha_1$, $\alpha_2$, $\alpha_3$, and $\alpha_4$ mentioned above are useful as defining standards in the context of the present account. These tests are defined in detail below.

Test $\alpha_1$ of DP stability to lyophilization/rehydration:

50 ml of a DP suspension at 0.2% by weight, calculated on the basis of the mass of polymer forming the DP, are prepared in a 500 ml round-bottomed flask. The buffered saline aqueous phase used consists of 0.01 M PBS (phosphate buffer, pH 7.4 at 25° C.).

This solution is then frozen in liquid nitrogen before being lyophilized using a CHRIST-ALPHA1-4 brand lyophilization device, by subjecting the sample to a pressure of 20 Pa and a temperature of −52° C. for 48 h.

The lyophilizate thus obtained is then hydrated by placing it in the presence of a volume of aqueous phase identical to that used to make the suspension and representing 5 ml.

The particle size distribution of the DPs thus rehydrated is measured by laser scattering using a COULTER LS 130 machine according to a FRAUNHOFER calculation model with "PIDS". This allows the D[4.3] to be obtained.

The same particle size distribution measurement with determination of the D[4.3] is carried out on the DP suspension prepared above and the D[4.3] values obtained with and without lyophilization/rehydration are compared.

Test $\alpha_2$ of DP stability to centrifugation:

A DP suspension is prepared in the same way as in the text $\alpha_1$ described above, except that the DP concentration in the suspension is 2% by weight instead of 0.2%.

A sample of 1.5 ml of the abovementioned suspension is centrifuged using a SIGMA 3K30 brand centrifuge for 10 min at 60,000 g.

The sample is stirred manually in order to resuspend the DPs after centrifugation.

The particle size measurements (D[4.3]) are carried out as described in test $\alpha_1$ above. The D[4.3] values obtained before and after centrifugation are compared.

Test $\alpha_3$ of DP resistance to pH:

0.5 ml of DP suspension at 2% (concentration expressed in the same way as that given in test $\alpha_1$) is introduced into 5 ml of an HCl solution with a titer of $10^{-2}$ N (pH 2).

This mixture is stored for one day at ambient temperature.

The suspension is neutralized by introduction of 50 μl of 1 N sodium hydroxide. This mixture is made up to 10 ml with phosphate-buffered saline (PBS) solution, pH 7.4.

The D[4.3] particle size measurements are carried out on suspensions which have and have not had their pH lowered to a value of 2. The D[4.3] values obtained in the two cases are compared.

Exactly the same operation is carried out, but this time introducing 0.5 ml of DP suspension at 2% (concentration expressed in the same way as that given in test $\alpha_1$) in 5 ml of $10^{-1}$ N sodium hydroxide. The mixture is neutralized by addition of 0.5 ml of 1 N HCl. It is made up to 10 ml with isotonic phosphate-buffered saline (PBS) solution, pH 7.4.

The same measurements and the same particle size comparisons of D[4.3] are carried out.

Test $\alpha_4$ of DP stability on storage:

A DP suspension is prepared which is identical in all respects to the one prepared in accordance with test $\alpha_2$ described above.

Samples of this suspension (2 ml) are stored at temperatures of 2, 4 and 37° C. and at ambient temperature.

The particle size distribution and, in particular, the D[4.3] (same method of measurement as for the tests $\alpha_1$ to $\alpha_3$ above) are monitored as a function of the storage time.

The D[4.3] values obtained after different storage times under the different temperature conditions are compared with a D[4.3] reference measured on the suspension just after it has been prepared (t=0).

The storage time thresholds with conservation of the particle size distribution of the DPs are set arbitrarily as indicated below:

greater than or equal to three months at 37° C.;

greater than or equal to nine months at ambient temperature;

greater than or equal to eighteen months at 4° C.

Preferably, the composite gel DPs according to the invention have at least two of the functional characteristics $\alpha_1$, $\alpha_2$, $\alpha_3$ and $\alpha_4$, and even more preferably $\alpha_1$, $\alpha_2$ and $\alpha_3$.

These characteristics are illustrated below in the examples.

As indicated above, the selection of the copolyamino acid is one of the crucial parameters of the invention. Thus, in accordance with a preferred characteristic, the copolyamino acid (III) has:

comonomers $AA_i$ chosen from the following group of amino acids: glutamic acid, aspartic acid, ornithine, arginine, lysine, asparagine, histidine and mixtures thereof, as well as comonomers $AA_o$ chosen from the following group of amino acids: leucine, tyrosine, phenylalanine, valine, cystine, isoleucine and mixtures thereof., Even more preferably, the copolyamino acid (III) comprises a comonomer $AA_i$ formed of glutamic acid and/or aspartic acid, as well as a monomer $AA_o$ formed of leucine and/or isoleucine and/or tyrosine and/or phenylalanine.

The linear copolyamino acids (III) according to the invention can be of random structure or of diblock, triblock or multiblock structure, the diblock structure being preferred for reasons of non-immunogenicity.

The term random structure is understood to refer to a copolymer obtained from comonomers having different reactivity ratios, which implies that the composition of these so-called random copolymers varies as a function of the degree of conversion.

An example of a copolyamino acid (III) which is more specifically suited to the invention is Leu/Glu, and in particular the one with a 50/50 assay.

Limiting the number of comonomers to two amino acids, an $AA_O$ and an $AA_i$, minimizes the immunogenicity of the DPs. This is a considerable advantage of this preferred embodiment of the invention.

Besides their preferred linear structure containing α-peptide chains, the copolyamino acids (III) have, as another characteristic, a high molar mass $M_W$, i.e. greater than or equal to 5000 D, preferably between 8000 and 100,000 D. More preferably, the molar mass $M_W$ of the copolyamino acids (III) is selected as a function of their nature: multiblock or random. In the case of multiblock, in particular diblock, polyamino acids (III), the preferred ones are those with a mass $M_W$ of greater than or equal to 5000 D, preferably between 3000 and 100,000 D and even more preferably between 5000 and 20,000 D. As regards the copolyamino acids (III) of random type, those with an $M_w$ of greater than or equal to 50,000 D, preferably between 10,000 and 300,000 D and even more preferably between 10,000 and 100,000 D, are more preferably selected.

In fact, these copolyamino acids (III) are amphiphilic copolymers formed of a first type of monomers $AA_0$, which is a neutral hydrophobic amino acid, and of at least a second type of comonomers $AA_i$, which is an amino acid having a side chain of carboxyl functionality (Glu/Asp) which can be ionized at physiological pHs which do not denature proteins. These amphiphilic AAPs (III) can interact both with hydrophobic substances and with hydrophilic substances, which gives them noteworthy properties as surfactants or dispersants. They thus participate in the surprising effect by which the DPs acquire and conserve the quality of definite stable bodies.

As regards the availability of the APs (III), it should be pointed out that many techniques exist for the synthesis of block or random α-amino acid polymers or of multiple-chain polymers or alternatively of polymers containing a determined amino acid sequence (cf. Encyclopedia of Polymers Science and Engeneery [sic] (vol. 12, page 786, Ivan WILEY & Sons).

Many amino acid derivatives and peptides have been used as monomers for the preparation of polyamino acids. However, the monomers most frequently used are N-carboxy-α-amino acid anhydrides, the preparation of which is given, for example, in Biopolymers, 15, 1869 (1976). The techniques for polymerizing these monomers are known to those skilled in the art and are detailed in the book by H. R. KRICHELDORF "α-Aminoacid-N-Carboxy Anhydrides and Related Heterocycles" Springer Verlag (1987)

The synthetic techniques generally involve protecting the reactive functions of the amino acids with ionizable side chains, in order for them not to interfere during the polymerization step. Consequently, a deprotection step is necessary in order to reestablish the functionality of the ionizable side chains of the polymer. Mention may be made, for example, of processes of deprotection by saponification of methyl esters (STAHMAN et al.; J. Biol. Chem., 197, 771 (1952); KYOWA HAKKO, FR 2 152 582) or debenzylation [BLOUT et al.; J. Amer. Chem. Soc., 80, 4631 (1858 [sic])].

Now, as regards the oil (I), it may be indicated that, for the purposes of the invention, an oil denotes a substance which is liquid at ambient temperature and which, in addition, is immiscible or only sparingly miscible with water. Fatty substances which are liquid at ambient temperature satisfy this definition. This is likewise the case for silicone oils.

Thus, in accordance with a preferred characteristic of the invention, the oil (I) is formed of one or more fatty compounds selected from the following group:

medium-chain fatty ester acid triglyceride(s) of animal, plant or synthetic origin, paraffin(s), polysiloxane oil(s), fatty acids of animal or plant origin, fatty acids, esters thereof and/or salts thereof.

As examples of oils which are particularly suitable for the DPs according to the invention, mention may be made of triglyceride oils such as coconut oil (such as the one sold under the brand name "MYGLIOL®" by the company DYNAMIT NOBEL, corn oil, paraffin, olive oil, isopropyl palmitate, butyl stearate, ethyl oleate, eicosapentanoic docosahexanoic acid esters, alkyl benzoate, eicosapentanoic docosahexanoic acids, eicosapentanoic docosahexanoic acid triglycerides, caprylic acid triglycerides, silicone oil.

The oil (I) can consist of only one type of fatty substance which is liquid at ambient temperature or of a mixture of several of these.

According to a variant, the oil(s) (I) may or may not be fractionated. Fractionation makes it possible to remove certain fatty acid fractions, so as to modify the melting point and the viscosity.

As regards, more specifically, the melting point, it can be pointed out, in order to establish the ideas, that the melting point of the oil (I) is less than or equal to 50° C., preferably to 40° C. and, more preferably, to 35° C.

The viscosity of the oil (I) at 25° C. is, in practice, between 10 mPa.s and 3000 mPa.s.

In quantitative terms, the oil (I) represents from 9 to 90% by weight, preferably from 20 to 80% by weight and even more preferably from 40 to 60% by weight, of the DPs.

As regards the aqueous phase (II) of the lipid microparticles considered here, this preferably consists of a saline solution which will advantageously be buffered, so as to have a pH of between 5 and 9, preferably between 6 and 8 and even more preferably of about 7.4.

The solutes in this solution are salts such as, for example, NaCl.

Advantageously, the molarity of the saline solution is between $10^{-4}$ M and 1 M, preferably between $10^{-2}$ M and 0.5 M approximately.

The buffers which may be used are, for example, the following: phosphate, phthalate, borate, etc.

The fact that the aqueous phase is preferably formed of a saline solution is not exclusive of the variant in which water, advantageously deionized water, is involved.

The preferred lipid microparticles according to the invention are those characterized by the following composition:

(I) medium-chain fatty ester acid triglyceride(s), coconut oil being particularly preferred, (II) deionized water or buffered saline solution, the pH of this aqueous phase being between 6 and 8, (III) copolyamino acid of Leu/Glu type, preferably 50/50.

Beyond the structural and functional characteristics of the DPs, such as those which have been mentioned above, the subject of the present invention is also a process for the preparation of microparticles, in particular such as those defined above, characterized in that it comprises, essentially, the following successive or non-successive steps:

-a- preparation of a gel from the aqueous phase (II) and of at least one copolyamino acid (III), (II) and (III) being as defined in the description, -b- placing the gel obtained from step -a- in contact with oil (I), as defined in the description, -c- stirring the gel+(I) mixture leading to a dispersion of microparticles in an oily or aqueous continuous phase (I), -d- optional separation of the microparticles and of the oily or aqueous continuous phase, preferably by centrifugation, -e- optional redispersion of the microparticles collected after step -e- in a storage liquid, -f- optional lyophilization treatment of the microparticles from step -d-, which are or are not redispersed.

One of the foundations of this process and of the microparticles arising therefrom concerns step -a- for the preparation of a gel derived from the combination of the copolyamino acid (III) and of the aqueous phase (II). This more specifically involves mixing (II) with (III) in proportions such that (III) represents from 2 to 50%, preferably from 5 to 30%, by weight of the gel (III)+(II). This mixing is carried out with stirring using any suitable stirring means known per se. This means can be, for example, a vortex type device or alternatively a rotor-stator, magnetic bar, ultrasound or high-pressure homogenizer type device.

Advantageously, this step -a- is combined with a treatment for removal of the foam formed during the stirring. Such a removal can be carried out, for example, by centrifugation.

The gel obtained in step -a- is then placed in contact with all or some of the oil (I) (step -b-), the mixture thus formed then being subjected to stirring (step -c-) with stirring means of the same type as those mentioned for step -a-. This step -c- corresponds to the step for the formation of the lipid microparticles.

The introduction of the oil (I) into the mixture from step -b- can be carried out one or more times during step -c-.

It is clear that the stirring conditions are determining factors for the formation of the DPs in step -c-, in particular with regard to the nature of the homogeneous phase containing the DPs: water or oil.

Thus, according to a preferred embodiment of the invention, leading to composite gel DPs suspended in an aqueous phase, this stirring -c- is carried out using a rotor/stator device and working at a stirring speed of between 1000 and 40,000 rpm, preferably 5000 and 25,000 rpm.

According to a variant of this preferred embodiment, which is aimed at obtaining DPs suspended in an oily phase, the suspension is enriched with oil.

At the end of step -c-, it is possible to obtain an interesting intermediate product, formed of a concentrated dispersion of DPs in water or a suspension of DPs in oil. In the latter case, the excess oil can be removed and a concentrated DP sedimentate is thus obtained.

The subject of the present invention is thus also this concentrated dispersion and this concentrated sedimentate of DPs in water, which can be considered as intermediate products.

These intermediate products are characterized by:

an average concentration of copolyamino acids (III) ranging from 1% to 50% by weight, preferably from 2% to 40% by weight, this concentration being established, even more preferably, from 3% to 30% by weight;

a concentration of oil (I) representing from 9 to 90% by weight, preferably from 20 to 80% by weight and even more preferably from 40 to 60% by weight;

a concentration of aqueous phase of from 5 to 90% by weight, preferably from 10 to 70% by weight, even more preferably from 30 to 50% by weight;

the above concentrations being expressed relative to the total mass of the concentrated DP dispersion or sedimentate.

The relative amounts of oil (I) and of aqueous phase (II) will override each other depending on the hydrophilic or hydrophobic nature intended for the DPs. In the biovector application, this nature will depend on the active principle to be delivered.

To summarize, it can thus be indicated that the microparticles according to the invention can be defined by the following quantitative characteristics, according to which their constituents (I), (II) and (III) are present in the proportions below, expressed as % by weight relative to (I)+(II)+(III):

(I) 9 to 90, preferably 20 to 80 and even more preferably 40 to 60, (II) 5 to 90, preferably 10 to 70 and even more preferably 30 to 50, (III) 1 to 50, preferably 2 to 20 and even more preferably 3 to 10.

The microparticles can be recovered (step -d-) by any suitable known means, centrifugation or decantation being examples of such means.

The medium for dispersing the DPs recovered in step -d- can be filtered deionized water or a buffered solid solution, to which at least one bacteriostatic agent may be added.

Advantageously, the temperature at which steps -a- to -c-, or even -d- to -f- of the process according to the invention are carried out is between 4° C. and 60° C. Ambient temperature is particularly appropriate, this preferably being between 10 and 35° C.

As emerges from the text hereinabove, the process according to the invention allows the spontaneous generation of lipid microparticles by means of a noteworthy, simple, cost-effective and thus industrially feasible procedure. It will also be noted that the process according to the invention is unquestionably and invariably safe, since it does not envisage using toxic solvents or reagents.

The important parameters of the process according to the invention are, in particular, the nature of the oil (I), the composition of the copolyamino acid (III) and its concentration, the concentration of the saline solution (II), the stirring conditions and the pH of the reaction medium.

A person skilled in the art is capable of relatively easily controlling all of these conditions for the preparation of the DPs according to the invention. In particular, it is entirely within his or her ability to control and adjust the particle size of the lipid microparticles by varying the stirring conditions and the ratio of the viscosities of the phases present, inter alia.

Since one of the most noteworthy applications of the particles according to the invention is the protected delivery of active principles (APs) into the human or animal body, it is worthwhile, at this stage in the account, providing details on the technique(s) for including the AP into the DPs.

One of the preferred inclusion techniques in accordance with the invention consists in dissolving or suspending the said AP:

in the oil (I), and/or in the aqueous phase (II), and/or in the polyamino acid (III), and/or in the gel from step -a-.

The AP to be included in the DPs can be in solid form or in the form of a solution or a dispersion.

The active principle which can be included or incorporated into the DPs according to the invention can be medicinal and/or nutritional. When it is medicinal, the AP is preferably chosen from:

proteins and/or peptides, among which those most preferably selected are: hemoglobins, cytochromes, albumins, interferons, antigens, antibodies, calatonin, erythropoietin, insulin, growth hormones, factor IX, interleukin or mixtures thereof, polysaccharides, heparin being more particularly selected, nucleic acids and, preferably, RNA and/or DNA oligonucleotides, and mixtures thereof.

The APs, which can be classified in the category of medicaments and which can be delivered by the particles according to the invention, are vaccines.

As examples of nutritional APs, mention may be made of vitamins, amino acids and trace elements.

INDUSTRIAL APPLICATION

According to another of its aspects, the invention is also directed towards use of DPs filled with AP, for the manufacture of medicaments, in particular of the type including a system with controlled release of AP.

Lastly, the present invention relates to the medicaments and the pharmaceutical and nutritional specialties comprising the microparticles filled with AP, as described above.

The pharmaceutical specialties concerned are, in particular, those preferably for oral, nasal, vaginal, ocular, subcutaneous, intravenous, intramuscular, intradermal, intraperitoneal, intracerebral or parenteral administration.

The applications of the invention are not limited to vectorization, to the delivery of an AP of medicinal or nutritional nature, since it is entirely conceivable that the AP, which can be included or incorporated into the DPs, might be a cosmetic or plant-protection product.

The cosmetic applications which can be envisaged are, for example, compositions which can be applied transdermally.

The plant-protection products concerned can be, for example, herbicides and/or fungicides and/or bactericides and/or virucides and/or insecticides, inter alia.

The subject of the present invention is also the plant-protection and cosmetic compositions comprising DPs filled with AP of the type referred to above.

The examples which follow will give a clearer understanding of the invention in its various product/process/application aspects. These examples illustrate the preparation of DP microparticles, which are or are not filled with active principles and based on oil (I), water (II) and AAP (III). These examples also show the structure characteristics, as well as the properties of the said microparticles.

The illustration of the examples is given by FIGS. 1 to 9 described below.

DESCRIPTION OF THE FIGURES

FIG. 7 is a histogram of voluminal distribution of composite gel DPs (differential volume (V) in % as a function of the diameter (D) in $\mu$m):

curve 1: before lyophilization/rehydration, curve 2: after lyophilization/rehydration (Example 7).

EXAMPLES

Example 1

50/50 Poly(LEUCINE-SODIUM GLUTAMATE)

Random Synthesis

STEP 1): COPOLYMERIZATION OF NCA-LEU AND NCA-GLU(OMe): 50/50 POLY(LEU-CO-GLU(OMe)):

15.0 g of methyl glutamate N-carboxyanhydride (NCA-Glu(OMe): 0.08 mol) and 12.5 g of leucine N-carboxyanhydride (NCA-Leu: 0.08 mol) are introduced, under a stream of nitrogen, into a 1 l reactor fitted with a glass stirrer, a nitrogen inlet and an outlet connected to a bubbler. 381 ml of dioxane are added and the reaction medium is brought to 40° C.

After dissolving the NCA, 24 ml of water are added, followed by 0.22 ml of triethylamine (i.e. 1 mol % relative to the NCA). The polymerization is monitored by IR by observing the disappearance of the carbonyl bands at 1860 and 1790 cm$^{-1}$. The polymerization time ranges between 1.5 h and 3 h depending on the composition of the monomers. After the bands have totally disappeared, the reaction medium is diluted with 380 ml of dioxane and then homogenized for 3 h at ambient temperature. The copolymer is recovered by precipitation from 5 l of water with vigorous stirring. The product is filtered off and dried at 50° C. under vacuum for 12 h.

The mass of copolymer obtained is 18.4 g, i.e. a weight yield of 90%.

$^1$H NMR (d-trifluoroacetic acid): 0.85 ppm (CH$_3$-Leu, 6H*0.5); 1.58 (CH$_2$ and CHMe$_2$ Leu, 3H*0.5); 2.10 and 2.22 (CH$_2$-Glu, 2H*0.5); 2.58 (CH$_2$-Glu; 2H*0.5); 3.75 (CH$_3$-Glu, 3H*0.5); 4.62 (NCHCO-Leu, 1H*0.5); 4.70 (NCHCO-Glu, 1H*0.5). Reduced viscosity (0.5 g/dl in trifluoroacetic acid) at 25° C.=2.2 dl/g.

STEP 2): HYDROLYSIS OF THE METHYL ESTER OF 50/50 POLY(LEU-CO-GLU(OMe)):

The copolymer obtained above (17.7 g) is placed in a reactor into which are added 354 ml of trifluoroacetic acid. The reaction medium is brought to 40° C. with stirring. When the copolymer has totally dissolved, 354 ml of water are added portionwise. The reaction medium is kept stirring for 48 h. The polymer is recovered by precipitation from 5 l of water. After filtration, it is again suspended and stirred in water for 0.5 h, and then filtered off and drained. The purification is carried out by dialysis in water. 15.9 g (95%) yield. $^1$H NMR (d-trifluoroacetic acid): identical to the starting polymers except that the signal at 3.75 ($CH_3$-Glu) is greatly reduced or absent. In the present case, the level of residual esters is less than 1% relative to the glutamate monomers. Reduced viscosity (0.5 g/dl in trifluoroacetic acid) at 25° C.=0.95 dl/g.

Example 2

Synthesis of the 50/50 Poly(LEU-B-GLU(ONa)) Diblock 15.0 g of NCA-Glu(OMe) (0.08 mol) and 180 ml of dioxane are introduced into a 1 l reactor with stirring. After dissolution, 180 ml of toluene are added and the medium is brought to 60° C. The IR spectrum of the solution is acquired, after which 0.156 g of benzylamine (1.58 mol %/NCA) is added. The reaction medium rapidly becomes cloudy and, after 40 minutes, the characteristic bands at 1860 and 1790 $cm^{-1}$ have disappeared.

After one hour, a solution of 12.5 g of NCA-Leu (0.08 mol) in a dioxane/toluene mixture (15 ml of each) is introduced. Stirring is continued for 18 h (this duration was not optimized). The carbonyl bands have by then disappeared.

100 ml of dioxane are added and the reaction medium is homogenized for 1 h. The copolymer is precipitated from 3 l of absolute ethanol with vigorous stirring. It is washed with 1 l of ethanol, filtered off, drained and finally dried at 50° C. after vacuum overnight.

The mass of product recovered is 19.5 g (yield=95%).
$^1$H NMR (d-trifluoroacetic acid): 0.85 ppm ($CH_3$-Leu, 6H*0.5); 1.58 ($CH_2$ and $CHMe_2$ Leu, 3H*0.5); 2.10 and 2.22 ($CH_2$-Glu, 2H*0.5); 2.58 ($CH_2$-Glu; 2H*0.5); 3.75 ($CH_3$-Glu, 3H*0.5); 4.62 (NCHCO-Leu, 1H*0.5); 4.70 (NCHCO-Glu, 1H*0.5). Reduced viscosity (0.5 g/dl in trifluoroacetic acid) at 25° C.=0.62 dl/g.

The second step for hydrolysis of the methyl esters is identical to that described in Example 1, step 2. 95% yield. $^1$H NMR (d-trifluoroacetic acid): identical to the starting polymers except that the signal at 3.75 ($CH_3$-Glu) is greatly reduced or absent,. In the present case, the level of residual esters is less than 1% relative to the glutamate monomers. Reduced viscosity (0.5 g/dl in trifluoroacetic acid) at 25° C.=0.55 dl/g.

Example 3

Synthesis of the 25/50/12 Poly(GLU(ONa)-LEU-GLU(ONa)) Triblock 7.5 g of NCA-Glu(OMe) (0.04 mol) and 180 ml of dioxane are introduced into a 1 l reactor with stirring. After dissolution, 180 ml of toluene are added and the medium is brought to 60° C. The IR spectrum of the solution is acquired, after which 0.156 g of benzylamine is added.

After the monomer has totally disappeared, a solution of 12.5 g of NCA-Leu (0.08 mol) in a dioxane/toluene mixture (15 ml of each) is introduced. Stirring is continued for 18 h. Next, a further 7.5 g of NCA-Glu(OMe) (0.04 mol) are added and are allowed to react for 12 hours. 100 ml of dioxane are added and the reaction medium is homogenized for 1 h.

The copolymer is precipitated from 3 l of absolute ethanol with vigorous stirring. It is washed with 1 l of ethanol, filtered off, drained and finally dried at 50° C. under vacuum overnight.

The mass of product recovered is 19.4 g (yield=95%).
$^1$H NMR (d-trifluoroacetic acid): 0.85 ppm ($CH_3$-Leu, 6H*0.5); 1.58 ($CH_2$ and $CHMe_2$ Leu, 3H*0.5); 2.10 and 2.22 ($CH_2$-Glu, 2H*0.37); 2.58 ($CH_2$-Glu; 2H*0.37); 3.75 ($CH_3$-Glu, 3H*0.37); 4.62 (NCHCO-Leu, 1H*0.5); 4.70 (NCHCO-Glu, 1H*0.37). Reduced viscosity (0.5 g/dl in trifluoroacetic acid) at 25° C.=0.58 dl/g.

The second step for hydrolysis of the methyl esters is identical to that described in Example 1, step 2. $^1$H NMR (d-trifluoroacetic acid): identical to the starting polymer except that the signal at 3.75 ($CH_3$-Glu) is greatly reduced or absent. In the present case, the level of residual esters is less than 1% relative to the glutamate monomers. Reduced viscosity (0.5 g/dl in trifluoroacetic acid) at 25° C.=0.38 dl/g.

Example 4

Neutral Microparticles Prepared from Miglyol®, Water and Poly(LEUCINE-CO-SODIUM GLUATMATE) of 50/50 Composition and of Random Structure 4.1—METHODOLOGY:
  4.1.1—STEP a):
PREPARATION OF THE GEL:
  50 mg of poly(leucine-CO-sodium glutamate) (abbreviated as Leu/Glu) lyophilizate, of
  50/50 composition, of random structure, synthesized according to Example 1 and with an $M_W$ of 110,000, are introduced into a hemolysis tube.
  The aqueous phase is added, typically 500 mg, which can be composed of deionized water or a buffered saline solution, for example 0.01 M PBS (phosphate buffer, pH 7.4 at 25° C.).
  The polyamino acid lyophilizate is left to become hydrated for 2 hours at ambient temperature.
  The gel obtained is in the form of a viscous colloidal solution which scatters in the blue region.
  4.1.2—STEPS b) to e):
PREPARATION OF THE MICROPARTICLES:
  (i) Process to obtain DPs in an oily continuous phase:
    2 ml of the lipid phase composed of fractionated coconut oil, known under the trade name Miglyol® (DYNAMIT NOBEL), are introduced into the hemolysis tube containing the polyamino acid gel.
    The mixture is stirred using a rotor/stator type homogenizer (ULTRA-TURRAX T8, TKA LABORTECHNIK). A milky-looking dispersion of microparticles in a lipidic continuous phase is obtained.
    The hemolysis tube containing the microparticle dispersion is centrifuged. The supernatant phase, composed of excess Miglyol®, is separated from the sedimentate by simply pouring it off. 1340 mg of oil are thus collected.
    The sedimentate is redispersed in deionized water containing a bacteriostat: Thimerosal® (50 µg/ml), or in a buffered saline solution, for example 0.01 M PBS (phosphate buffer, pH 7.4 at 25° C.) containing Thimerosal® (50 µg/ml). The total volume of the dispersion obtained is 5000 µl.

(II) Process to obtain DPs in an aqueous continuous phase:

400±2 µl of the lipid phase, composed of fractionated coconut oil known under the trade name Miglyol® (DYNAMIT NOBEL), are introduced into the hemolysis tube containing the polyamino acid gel.

The mixture is stirred with a rotor/stator type homogenizer (ULTRA-TURRAX T8, IKA LABORTECHNIK). A very dense milky dispersion of microparticles in a continuous water phase is obtained.

The dispersion is then diluted in deionized water containing Thimerosal® (50 µg/ml), or in a buffered saline solution, for example 0.01 M PBS (phosphate buffer, pH 7.4 at 25° C.) containing Thimerosal® (50 µg/ml). The total volume of the dispersion obtained is 5000 µl.

4.2—CHARACTERIZATION OF THE MICROPARTICLES:

The overall composition of the microparticles before redispersion is:
4% polyamino acid,
53% Miglyol®,
43% water or saline solution.

Figure 3:
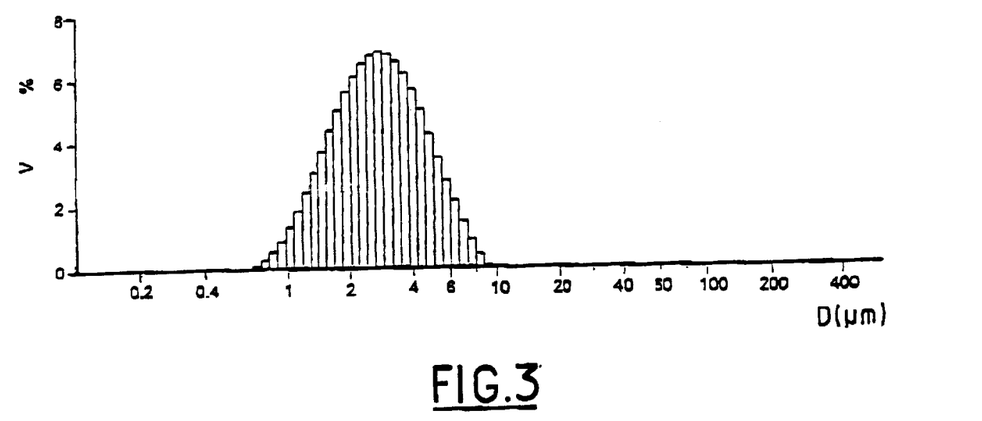
FIG. 3 is a histogram of voluminal distribution of composite gel DPs: differential volume (V) in % as a function of the diameter (D) in $\mu$m (Example 4).

The particle size distribution of the microparticles is measured by laser scattering. The machine used is a COULTER LS 130 machine. The calculation model chosen is the FRAUNHOFER model with "PIDS". The voluminal distribution histogram is given in FIG. 3. The profile is monomodal, the average reference diameter D[4.3] is 2.8 µm with a standard deviation (SD) of 1.1 µm. Expressed differently, the particle size distribution is as follows:

| % of DP: | 10.00 | 25.00 | 50.00 | 75.00 | 90.00 |
|---|---|---|---|---|---|
| Size in µm less than: | 5.165 | 3.876 | 2.730 | 1.901 | 1.394 |

The microparticles were observed by scanning electron microscopy (SEM) on a cold stage. The photographs are given [lacuna] FIG. 1.

The microparticles conserve their identity and their integrity in the solvents, such as acetone, dimethyl sulfoxide and ethanol, and in aqueous media over the pH range between pH=2 and pH=13.

Figure 4:
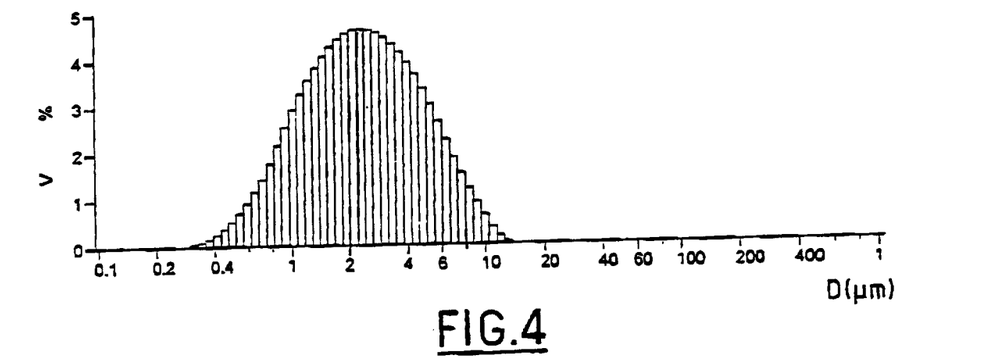
FIG. 4 is a histogram of voluminal distribution of lyophilized and rehydrated composite gel DPs: differential volume (V) in % as a function of the diameter (D) in $\mu$m (Example 4).

Test $\alpha_1$: Lyophilization/rehydration:

The suspension, diluted in 50 ml, is lyophilized for 48 h. 529 mg of microparticle lyophilizate are recovered. Rehydration of all the lyophilizate in 5 ml of PBS leads spontaneously to a suspension of microparticles having a monomodal particle size profile similar to that of the microparticles before lyophilization (cf. FIG. 4). The average voluminal diameter, D[4.3], is 2.9 µm and the standard deviation is 2 µm, i.e. a Δ of 3.5% relative to the reference D[4.3].

Test $\alpha_1$: Results:

| % of DP: | 10 | 25 | 50 | 75 | 90 |
|---|---|---|---|---|---|
| Size in µm less than: | 0.907 | 1.385 | 2.322 | 3.873 | 5.816 |

Test $\alpha_2$:
A D[4.3] of 3 µm is found with an estimation of the standard deviation of 2 µm, i.e. a Δ of 7.1% relative to the reference D[4.3].

Test $\alpha_3$:
at pH 2, a D[4.3] of 3.9 µm with an SD of 2.9 µm is measured, i.e. a Δ of 3.5% relative to the reference D[4.3],
at pH 13, a D[4.3] of 3.0 µm with an SD of 2.2 µm is measured, i.e. a Δ of 7.1% relative to the reference D[4.3].

Test $\alpha_4$:
The shape stability of the microparticles stored in aqueous or saline dispersion, at 4° C., 37° C. and at ambient temperature, is analyzed by monitoring the particle size of the microparticles. The microparticles are considered as being physically stable when the recorded change in the average diameter D[4.3] does not exceed more than 20% of the initial D[4.3].

Test $\alpha_4$: results:

| Storage temperature | 4° C. | Ambient temperature | 37° C. |
|---|---|---|---|
| Stability in aqueous dispersion | | >1 year | |
| Stability in saline dispersion | >6 months | | >3 months |

Example 5

Neutral Nanoparticles Prepared from Miglyol®, Water and Poly(LEUCINE-CO-SODIUM GLUTAMATE) of 50/50 Composition and of Random Structure 5.1—METHODOLOGY:

5.1.1—STEP a):

PREPARATION OF THE GEL:

The process is performed according to Example 4.1.1, using a mass of 150 mg of the polyamino acid mentioned above. The aqueous phase is thus typically 1350 mg.

5.1.2—STEP b) to e):

PREPARATION OF NANO-PARTICLES

1200 µl of Miglyol® are introduced into the test tube containing the polyamino acid gel.

The mixture is stirred with a rotor/stator type homogenizer (ULTRA-TURRAX T8, IKA LABORTECHNIK). A concentrated, viscous aqueous suspension of micro-capsules is thus obtained.

This suspension is diluted in a total volume of 15 ml of deionized water or of phosphate-buffered isotonic solution at pH 7.4.

The dilute suspension of microparticles is placed in the reservoir of a high-pressure homogenizer such as the MICROFLUIDICS brand Microfluidizer M-110S.

The dilute suspension of microparticles is homogenized for 10 min, applying an inlet pressure of about 5 bar to the pump.

A suspension of nanoparticles is thus collected on draining the reservoir.

5.2—CHARACTERIZATION OF THE NANOPARTICLES:

The overall composition of the nanoparticles before dilution is: 6% polyamino acid; 43% Miglyol®; 51% water or saline solution.

Figure 5:
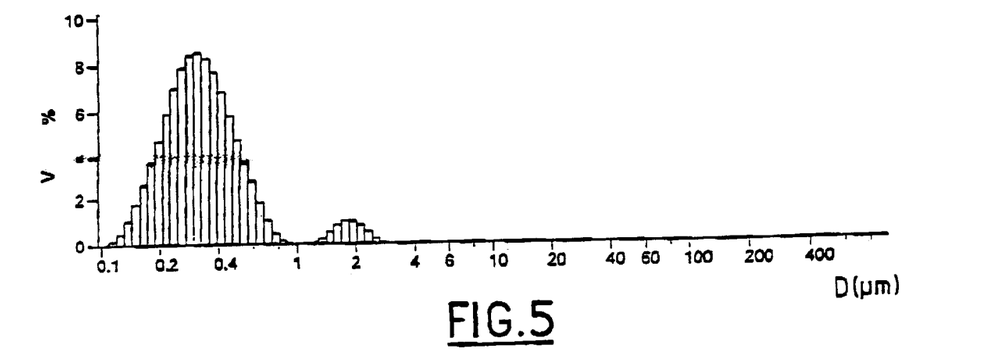
FIG. 5 is a histogram of voluminal distribution of composite gel DPs: differential volume (V) in % as a function of the diameter (D) in $\mu$m (Example 5).

The particle size distribution of the microparticles is measured by laser scattering. The machine used is a COULTER LS130 machine; the calculation model chosen is the Psl O.M.D. model with "PIDS". The voluminal distribution histogram is given in FIG. 5. The average reference diameter D[4.3] is 0.420 µm with a standard deviation of 0.37 µm.

| % of DP: | 10 | 25 | 50 | 75 | 90 |
|---|---|---|---|---|---|
| Size in µm less than: | 0.191 | 0.242 | 0.321 | 0.434 | 0.592 |

Test $\alpha_2$:

A D[4.3] of 0.45 µm and an SD of 0.41 µm are obtained, i.e. a Δ of 7.1% relative to the reference D[4.3].

Example 6

Neutral Microparticles Prepared from Miglyol®, Water and Poly(LEUCINE-CO-SODIUM GLUTAMATE) of 50/50 Composition and of Diblock Structure 6.1—METHODOLOGY:

6.1.1—STEP a):

PREPARATION OF THE GEL:

146 mg of poly(leucine-co-sodium glutamate) (abbreviated as LEU/GLU) lyophilizate synthesized according to Example 2 are introduced into a hemolysis tube.

The aqueous phase is added, typically 702±0.2 mg, which can be composed of deionized water filtered to 0.2 µm, or a buffered saline solution, for example 0.01 M PBS (phosphate-buffered isotonic solution at pH 7.4 at 25° C.).

The polyamino acid lyophilizate is left to become hydrated.

The gel obtained is in the form of a viscous colloidal solution which scatters strongly in the white region.

6.1.2—STEPS b) to e):

PREPARATION OF THE MICROCAPSULES:

The process is then performed as in Example 4.1.2(i). After centrifugation, 1518 mg of oil are collected.

6.2—CHARACTERIZATION OF THE MICROCAPSULES:

The overall composition of the microparticles before redispersion is: 12% polyamino acid; 31% Miglyol®; 57% water or saline solution.

Figure 6:
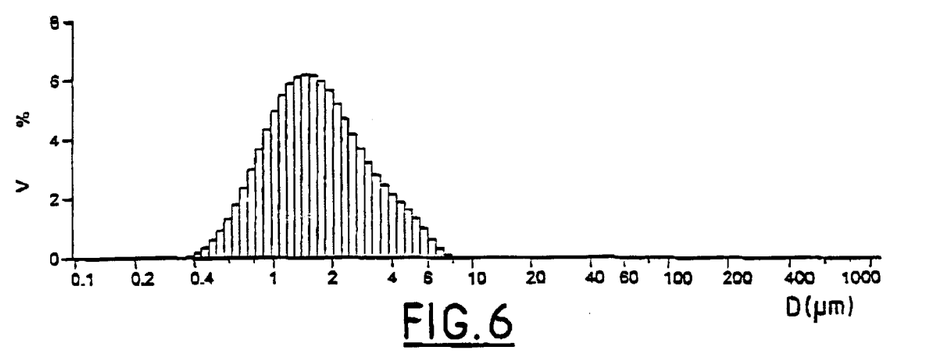
FIG. 6 is a histogram of voluminal distribution of composite gel DPs: differential volume (V) in % as a function of the diameter (D) in $\mu$m (Example 6).

The particle size distribution of the microparticles is measured by laser scattering. The machine used is a COULTER LS130 machine; the calculation model chosen is the FRAUNHOFER model with "PIDS". The voluminal distribution histogram is given in FIG. 6.

The profile is monomodal, the average reference diameter D[4.3] is 1.9 µm with a standard deviation of 1.2 µm.

| % of DP: | 10 | 25 | 50 | 75 | 90 |
|---|---|---|---|---|---|
| Size in µm less than: | 0.801 | 1.096 | 1.605 | 2.433 | 3.678 |

The microparticles were observed by SEM on a cold stage. The photographs are given in FIG. 2.

Test $\alpha_4$:

A Δ for the D[4.3] of less than or equal to 10%, relative to the reference D[4.3], is obtained.

Test $\alpha_4$—Results:

| Storage temperature | 4° C. | Ambient temperature | 37° C. |
|---|---|---|---|
| Stability in saline dispersion | ≧18 months | ≧12 months | ≧3 months |

Example 7

Neutral Microparticles Prepared from Miglyol®, Water and Poly(LEUCINE-CO-SODIUM GLUTAMATE) of 30/70 Composition and of Random Structure 7.1—METHODOLOGY:

7.1.1—STEP a):

PREPARATION OF THE GEL:

100 mg of poly(leucine-co-sodium glutamate) (abbreviated as LEU/GLU) lyophilizate of 30/70 composition, synthesized according to the procedure given in Example 1, changing the monomer ratio, are introduced into a hemolysis tube.

The aqueous phase is added, typically 400 mg, of 0.01 M PBS (phosphate-buffered isotonic solution at pH 7.4 at 25° C.).

The polyamino acid lyophilizate is left to become hydrated.

The gel obtained is in the form of a viscous colloidal solution which scatters in the blue region.

7.1.2—STEP b) to e):

PREPARATION OF THE MICROCAPSULES:

The process is performed as described in Example 4.1.2 (i). After centrifugation, 1620 mg of oil are collected.

7.2—CHARACTERIZATION OF THE MICROCAPSULES:

The overall composition of the microparticles before redispersion is: 12% polyamino acid; 38% Miglyol®; 50% saline solution.

Figure 8:
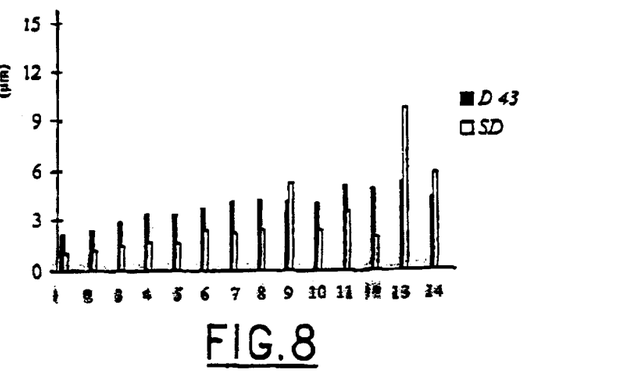
FIG. 8 represents a histogram giving the average diameters D[4.3] by volume and the standard deviations (SD) measured for the DP particle size distributions according to Tests 1 to 14 of Example 9.

The particle size distribution of the microparticles, measured by laser scattering under the standard conditions stipulated in Example 4, gives an average reference diameter D[4.3] of 2.9 µm with a standard deviation of 1.5 µm (cf. FIG. 8, curve 1).

Figure 7:
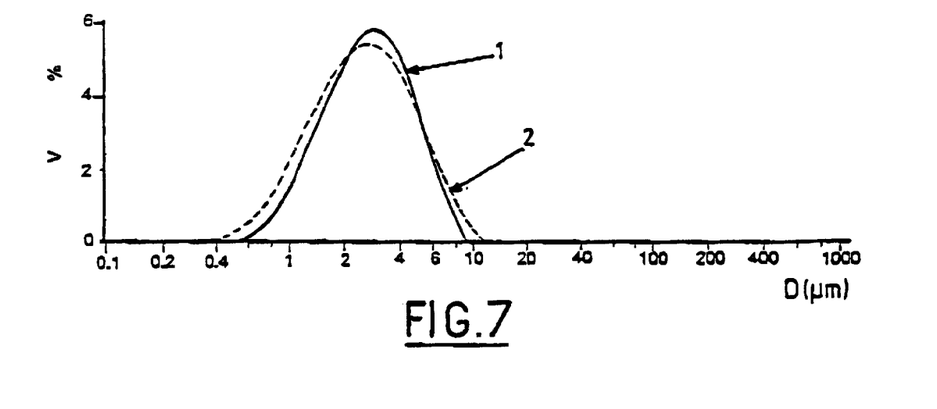

LYOPHILIZATION/REHYDRATION:

Test $\alpha_1$:

The dispersion of microparticles, thus obtained and characterized, is lyophilized for 48 hours. 212 mg of microparticle lyophilizate are recovered. Rehydration of all of this lyophilizate in 5 ml of PBS leads spontaneously to a microparticle suspension having a particle size profile which is virtually superimposable on the one before the lyophilization step. The D[4.3] is 3.0 μm with a standard deviation of 1.8 μm (cf. FIG. 7, curve 2), i.e. a Δ D[4.3], relative to the reference D[4.3], of 3.4%.

Example 8

Neutral Microparticles Prepared from Silicone Oil, Water and Poly(LEUCINE-CO-SODIUM GLUTAMATE) of 30/70 Composition and of Random Structure 8.1—METHODOLOGY:

8.1.1—STEP a):

PREPARATION OF THE GEL:

50 mg of poly(leucine-co-sodium glutamate) (abbreviated as LEU/GLU) lyophilizate of 30/70 composition, synthesized according to the procedure given in Example 1, changing the monomer ratio, are introduced into a hemolysis tube.

The aqueous phase is added, typically 450 mg, of 0.01 M PBS (phosphate-buffered isotonic solution at pH 7.4 at 25° C.).

The polyamino acid lyophilizate is left to become hydrated. v

The gel obtained is in the form of a viscous colloidal solution which scatters in the blue region.

8.1.2—STEP b) to e):

PREPARATION OF THE MICROCAPSULES:

2000 μl of silicone oil of reference code Rhodorsil® 47V20 are introduced into the hemolysis tube containing the polyamino acid gel.

The mixture is stirred with a rotor/ stator type homogenizer (ULTRA-TURRAX T8, IKA LABORTECHNIK). A milky-looking dispersion of microparticles in an oily continuous phase is obtained.

The hemolysis tube containing the microparticle dispersion is centrifuged (20 min at 3500 rpm). The supernatant phase, composed of excess silicone oil, is separated from the sedimentate by simply pouring it off; 921 mg of oil are thus collected.

The sedimentate is redispersed in deionized water containing Thimerosal® (50 μg/ml) or in a buffered saline solution, for example 0.01 M PBS (phosphate buffer, pH 7.4 at 25° C.) containing Thimerosal® (50 μg/ml). The total volume of the dispersion obtained is 5000 μl.

8.2—CHARACTERIZATION OF THE MICROCAPSULES:

The overall composition of the micro-particles before redispersion is: 3.3% polyamino acid; 66.6% Rhodorsil®; 30.1% saline solution.

The particle size distribution of the microparticles, measured by laser scattering under the standard conditions stipulated in Example 4, gives an average diameter D[4.3] of 4.7 μm with a standard deviation of 1.7 μm.

Example 9

Neutral Microparticles Prepared from Oils of Different Nature, Water and Poly(LEUCINE-CO-SODIUM GLUTAMATE) of 50/50 Composition and of Random Structure 9.1—METHODOLOGY:

The process is performed as indicated in Example 8 and the following oils are used:

| TEST | COMMON NAME | TRADE NAME | SUPPLIER |
|---|---|---|---|
| 1 | oleyl alcohol | NOVOL | CRODA |
| 2 | eicosapentanoic docosahexanoic acid triglyceride | INCROMEGA TG | CRODA |
| 3 | caprylic capric acid triglyceride | MIGLYOL | HULS |
| 4 | caprylic acid triglyceride | TRICAPRYLIN C8 | SIGMA |
| 5 | triglyceride of caprylic acid triglycerides [sic] | CRODAMOL GTCC | CRODA |
| 6 | alkyl benzoate | CRODAMOL AB | CRODA |
| 7 | isopropyl palmitate | CRODAMOL IPP | CRODA |
| 8 | butyl stearate | CRODAMOL BS | CRODA |
| 9 | eicosapentanoic docosahexanoic acid esters | INCROMEGA E | CRODA |
| 10 | ethyl oleate | ETHYL OLEATE | CRODA |
| 11 | liquid paraffin | C16/C21 fraction | MOREL/SALABE |
| 12 | silicone oil | RHODORSIL 47V100 | RHONE POULENC |
| 13 | olive oil | REFINED OLIVE OIL | CRODA |
| 14 | eicosapentanoic docosahexanoic acids | INCROMEGA F | CRODA |

9.2—CHARACTERIZATION OF THE MICROCAPSULES:

The overall composition of the micro-particles, before redispersion, varies depending on the lipid phases used, within the following ranges: 3 to 4% polyamino acid; 64 to 69% oil; 28 to 32% water or saline solution. Only the microparticles based on INCROMEGA E show a different composition before redispersion: 5% polyamino acid; 51% oil; 44% water or saline solution.

The particle size distributions of the microparticles are measured by laser scattering. The machine used is a COULTER LS130 machine; the calculation model chosen is the FRAUNHOFER model with "PIDS". The average voluminal diameters, D[4.3], and the standard deviations obtained are given on the graph in FIG. 8.

Example 10

Neutral Microparticles Prepared from Miglyol®, Water and Various Copoly(α-AMINO ACIDS) of Random Structure 10.1—METHODOLOGY:

The process is performed as mentioned in Example 4.1.1 and 4.1.2(i). The copoly(α-amino acids) used are those given in the table below. The hydration time of the lyophilizate of polymer in the isotonic solution (0.01 M PBS buffered to pH 7.4) is 24 hours. The gels obtained have different viscosities.

| No. | COPOLY(α-AMINO ACIDS) | SUPPLIER |
|---|---|---|
| 1 | 80/20 Poly(Glu; Phe) | SIGMA |
| 2 | 80/20 Poly(Glu/Leu) | SIGMA |
| 3 | 50/50 Poly(Glu/Tyr) | SIGMA |
| 4 | 25/75 Poly(Glu/Leu) | FLAMEL TECHNOLOGIES |
| 5 | 50/50 Poly(Orn/Leu) | SIGMA |

10.2—CHARACTERIZATION OF THE MICROPARTICLES:

The overall composition of the micro-particles, before redispersion, varies depending on the polymers used, within the following ranges:

| No. | % WATER | % MYGLIOL | % POLYMER |
|---|---|---|---|
| 1 | 20 | 77 | 3 |
| 2 | 33 | 62 | 5 |
| 3 | 51 | 43 | 6 |
| 4 | 39 | 56 | 5 |
| 5 | 27 | 68 | 5 |

The particle size distributions of the microparticles are measured by laser scattering. The machine used is a COULTER LS130 machine; the calculation model chosen is the FRAUNHOFER model with "PIDS". The average voluminal diameters, D[4.3], and the standard deviations (SD) obtained are given in the table below:

| No. | D[4.3] μm | SD μm | DISTRIBUTION PROFILE |
|---|---|---|---|
| 1 | 5.5 | 3.6 | monomodal |
| 2 | 8.8 | 8.6 | bimodal |
| 3 | 155.5 | 114 | monomodal |
| 4 | 5.9 | 3.9 | monomodal |
| 5 | 9.7 | 11.0 | bimodal |

The microparticles of batches 1 to 5 satisfy test $\alpha_2$:

Example 11

Microparticles Containing Cytochrome, Prepared from Miglyol®, Water and Poly(LEUCINE-CO-SODIUM GLUTAMATE) of 50/50 Composition and of Random Structure—DIRECT Encapsulation 11.1—METHODOLOGY:

Three batches of microcapsules were manufactured according to the identical operating conditions described below.

11.1.1—STEP a):
PREPARATION OF THE GEL:

1.5 ml of a stock solution of horse heart cytochrome C (ref. C2506 SIGMA) at 60 mg/ml in 0.01 M isotonic phosphate buffer (PBS), pH 7.4, are prepared.

50±0.2 mg of poly(leucine-co-sodium glutamate) (abbreviated as LEU/GLU) lyophilizate of 50/50 composition, of random structure and with an $M_W$ of 110,000, are introduced into a hemolysis tube.

450 mg of the cytochrome stock solution are added.

The polyamino acid lyophilizate is left to become hydrated.

The gel obtained is in the form of a viscous orange/red colloidal solution.

11.1.2—STEPS b) to e):
PREPARATION OF THE MICROCAPSULES ACCORDING TO THE PROCEDURE OF EXAMPLE 4.1.2(i):

2000 μl of Miglyol® (DYNAMIT NOBEL) are introduced into the hemolysis tube containing the polyamino acid gel and cytochrome.

The mixture is stirred with a rotor/stator type homogenizer (ULTRA-TURRAX T8, IKA LABORTECHNIK). A milky-looking dispersion of microparticles in a lipidic continuous phase is obtained.

The hemolysis tube containing the microparticle dispersion is centrifuged. The supernatant phase, composed of excess Miglyol®, is separated from the sedimentate by simply pouring it off. 1577 mg of oil are thus collected.

The sedimentate is redispersed in PBS filtered to 0.22 μm containing Thimerosal® (50 μg/ml). The total volume of the dispersion obtained is 20 ml.

Storage of the microparticle dispersion in a ventilated chamber conditioned to a temperature of 37° C.

11.2—CHARACTERIZATION OF THE MICROPARTICLES:

The overall composition of the three batches of microparticles before redispersion ranges from: 5±1% polyamino acid; 39±3% Miglyol®; 55±3% PBS.

The particle size distribution of the microparticles, measured by laser scattering on a COULTER LS130 machine in FRAUNHOFER mode with "PIDS" is monomodal for the three batches, with an average voluminal diameter D[4.3] of 2.4±0.5 μm and a standard deviation of 1.1±0.4 μm.

11.3—STUDY OF RELEASE:

To study the release, a known volume of microparticle dispersion is filtered at a given time. The filtrate is then analyzed by HPLC to assay the cytochrome released or not encapsulated. The filtrations were carried out at $T_0$ and then after 3 hours, 5 hours, 17 hours, 24 hours and 5 days of storage at 37° C.

FILTRATION CONDITIONS:

Stirred diafiltration cell of AMICON type, with a capacity of 50 ml.

Polysulfone type membrane (ref. XM 300, AMICON).
ASSAY CONDITIONS:
Affinity-separation HPLC on PLRPS column (300 A).
RESULTS:

The encapsulation yields, defined as the ratio of the amount of cytochrome encapsulated to the amount of cytochrome initially introduced, are 100%, for a cytochrome/polymer degree of encapsulation of 35%.

Figure 9:
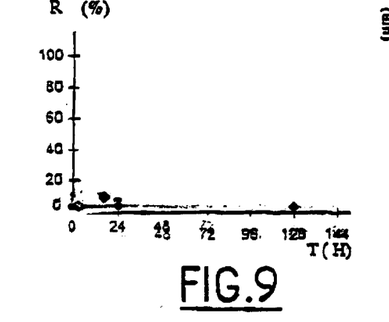
FIG. 9 is a graph giving the percentage R of release of the AP=cytochrome as a function of the residence time T in hours (Example 11).

No release R of cytochrome into the dispersion medium is observed after 5 days of storage at 37° C. (cf. FIG. 9).

Example 12

Microparticles Containing Cytochrome, Prepared from Miglyol®, Water and Poly(LEUCINE-CO-SODIUM GLUTAMATE) of 50/50 Composition and of Random Structure—Encapsulation by Self-assembly 12.1—METHODOLOGY:

A batch of microcapsules was manufactured according to the operating conditions described in Example 4.1.1 and 4.1.2(i). The micro-particle sedimentate is then dispersed in a volume of 10 ml of phosphate-buffered isotonic solution at pH 7.4 containing 1.0 mg/ml of horse heart cytochrome C. After a contact time of 24 h at ambient temperature, the microcapsule dispersion is filtered according to the conditions given in Example 11. HPLC analysis reveals a free cytochrome concentration of 0.5 mg/ml in the filtrate.

12.2—RESULT:

The degree of encapsulation of cytochrome is 10% relative to the polymer, for an encapsulation yield of 50%.

Example 13

Microparticles Containing a Protein "OSP A" Which is an Antigen for Lyme's Disease, Prepared from Miglyol®, Water and Poly(EUCINE-CO-SODIUM GLUTAMATE) [sic] of 50/50 Composition and of Random Structure: Direct Encapsulation 13.1—METHODOLOGY:

13.1.1—STEP a):

PREPARATION OF THE GEL:

50 mg of poly(leucine-co-sodium glutamate) (abbreviated as LEU/GLU) lyophilizate synthesized according to Example 1 are introduced into a hemolysis tube.

450 mg of an aqueous solution containing 4.4 mg/ml of Osp A are added.

13.1.2—STEPS b) to e):

PREPARATION OF THE MICROCAPSULES:

These steps are carried out in the same way as that described for the process of Example 4.1.2(i).

FILTRATION:

A volume of 2 ml of microcapsule dispersion is introduced into an ultrafiltration tube of ULTRAFREE XM300 type, sold by MILLIPORE.

After centrifugation, 1 ml of filtrate is collected and is analyzed by ELISA assay.

13.2—RESULT:

The ELISA assay reveals an unencapsulated Osp A concentration of 0.21 mg/ml in the filtrate.

The degree of encapsulation of Osp A is 0.36% relative to the polymer, for an encapsulation yield of 46%.

Example 14

Microparticles Containing a Glycoprotein "gD2t" Which is an Antigen for the Herpes Disease, Prepared from Miglyol®, Water and Poly (LEUCINE-CO-SODIUM GLUTAMATE) of 50/50 Composition and of Random Structure—Direct Encapsulation 14.1—METHODOLOGY 14.1.1—STEP a):

PREPARATION OF THE GEL:

50 mg of poly(leucine-co-sodium glutamate) (abbreviated as LEU/GLU) lyophilizate according to Example 1 are introduced into a hemolysis tube.

450±0.2 mg of an aqueous solution containing 0.666 mg/ml of gD2t are added.

14.1.2—STEPS b) to e):

PREPARATION OF THE MICROCAPSULES:

These steps are carried out in the same way as that described for the process with emulsion inversion in Example 4.1.2(i).

FILTRATION:

A volume of 2 ml of microcapsule dispersion is introduced into an ultra-filtration tube of ULTRAFREE XM300 type, sold by MILLIPORE.

After centrifugation, 1 ml of filtrate is collected and analyzed by ELISA assay.

14.2—results:

the elisa assay reveals an unencapsulated gg2t [sic] concentration of 5 $\mu$g/ml in the filtrate.

the degree of encapsulation of "gd2t" is 0.12% relative to the polymer, for an encapsulation yield of 92%.

What is claimed is:

1. Microparticles for use as active principle vectors, comprising:

a cohesive structure made of a physicochemically stable and integral composite gel comprising oil, an aqueous phase, and at least one linear, noncrosslinked, synthetic copolyamino acid comprising at least two different types of amino acid comonomers, a hydrophilic comonomer $AA_i$ and a hydrophobic comonomer $AA_0$, said microparticles having an average size which is controllable and adjustable over a range less than or equal to 500 $\mu$m.

2. Microparticles according to claim 1, wherein said cohesive structure is reflected by at least one of the properties:

a) absence of coalescence of the microparticles after a lyophilization treatment, this non-coalescence being reflected by a conservation of the particle size distribution, in particular of the D[4.3] in a proportion of ±20%, after rehydration according to a test $\alpha_1$;

b) absence of coalescence on centrifugation, reflected by a conservation of the particle size distribution, and in particular of the D[4.3] in a proportion of ±20%, according to a test $\alpha_2$;

c) resistance to pH variations, reflected by a conservation of the particle size distribution of the microparticles and, in particular, of the D[4.3] in a proportion of ±20%, after exposure to pHs of 2 to 13, according to a test $\alpha_3$;

d) absence of coalescence in dispersion in a buffered saline solution, reflected by a conservation of particle size distribution of the microparticles, in particular of their D[4.3] in a proportion of ±20%, for storage times of greater than or equal to 3, 9 and 18 months at temperatures of 37° C., ambient and 4° C. respectively, according to a test $\alpha_4$.

3. Microparticles according to claim 1, wherein the copolyamino acid comprises:

comonomers $AA_i$ selected from the group of consisting of glutamic acid, aspartic acid, ornithine, arginine, lysine, asparagine, histidine and mixtures thereof, comonomers $AA_0$, selected from the group consisting of leucine, tyrosine, phenylalanine, valine, cystine, isoleucine and mixtures thereof.

4. Microparticles according to claim 3, wherein $AA_i$=Glu and/or Asp and $AA_0$=Leu and/or isoleucine, and/or Tyr and/or Phe.

5. Microparticles according to claim 1, wherein the copolyamino acid is of random structure or of diblock, triblock or multiblock structure.

6. Microparticles according to claim 1, wherein the copolyamino acid is either multiblock and has a molar mass Mw of greater than or equal to 5000 D, or random and has a molar mass Mw of greater than or equal to 50,000 D.

7. Microparticles according to claim 1, wherein the oil is formed of at least one fatty compound selected from the group consisting of a medium-chain fatty ester acid triglyceride of animal, plant or synthetic origin, paraffin, polysiloxane oil, a fatty acid of animal or plant origin, and a fatty acid ester and/or salts thereof.

8. Microparticles according to claim 1, wherein the aqueous phase comprises a saline solution.

9. Microparticles according to claim 1, comprising:

at least one medium-chain fatty ester acid triglyceride, deionized water or buffered saline solution as the aqueous phase, the pH of the aqueous phase being between 6 and 8, copolyamino acid of Leu/Glu type.

10. Process for the preparation of microparticles according to claim 1, comprising the steps of:
   a) preparing a gel from the aqueous phase and at least one said copolyamino acid;
   b) placing the gel obtained from step a) in contact with at least one said oil to form a mixture;
   c) stirring the gel and oil mixture to form a dispersion of microparticles in an oily or aqueous continuous phase;
   d) optionally separating the microparticles and the oily or aqueous continuous phase;
   e) optionally redispersing the separated microparticles in a storage liquid; and
   f) optionally lyophilizing the microparticles from step d) or redispersed microparticles of step e).

11. Process according to claim 10, wherein step a) comprises mixing the aqueous phase and the at least one copolyamino acid in proportions such that the at least one copolyamino acid represents from 2 to 50% by weight of the gel formed in step a).

12. Process according to claim 10, wherein during step c), the oil is introduced into the mixture from step b).

13. Process according to claim 10, wherein the stirring is carried out using a rotor/stator device and working at a stirring speed of between 1000 and 40,000 rpm.

14. Process according to claim 10, carried out at between 10 and 35° C.

15. Process according to claim 10, wherein at least one active principle is incorporated into the oil and/or into the aqueous phase and/or into the at least one copolyamino acid and/or into the gel from step a), so as to obtain microparticles filled with the at least one active principle.

16. Microparticles according to claim 1, comprising at least one active principle which is medicinal and is selected from the group consisting of proteins, peptides, polysaccharides and nucleic acids.

17. Microparticles according to claim 1, comprising an active principle which is at least one vaccine.

18. Pharmaceutical specialty for oral, nasal, vaginal, ocular, subcutaneous, intravenous, intramuscular, intradermal, intraperitoneal, intracerebral or parenteral administration, comprising microparticles according to claim 1.

19. Microparticles according to claim 1, comprising at least one active principle which is a plant protection or cosmetic product.

20. Microparticles according to claim 6, wherein the copolyamino acid is multiblock and has a molar mass between 5000 and 100,000 D.

21. Microparticles according to claim 1, of a size between 0.05 and 100 $\mu$m.

* * * * *